US009396395B2

(12) United States Patent
Goto

(10) Patent No.: US 9,396,395 B2
(45) Date of Patent: Jul. 19, 2016

(54) IMAGE PROCESSING APPARATUS AND IMAGE PROCESSING METHOD, CONFIGURED TO APPLY THRESHOLD CONDITIONS TO SPECIFY TARGET PIXEL

(71) Applicant: HITACHI MEDICAL CORPORATION, Tokyo (JP)

(72) Inventor: Yoshihiro Goto, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 0 days.

(21) Appl. No.: 14/408,362

(22) PCT Filed: Aug. 27, 2013

(86) PCT No.: PCT/JP2013/072802
§ 371 (c)(1),
(2) Date: Dec. 16, 2014

(87) PCT Pub. No.: WO2014/038428
PCT Pub. Date: Mar. 13, 2014

(65) Prior Publication Data
US 2015/0235085 A1 Aug. 20, 2015

(30) Foreign Application Priority Data
Sep. 7, 2012 (JP) ................. 2012-197462

(51) Int. Cl.
G06K 9/00 (2006.01)
G06T 7/00 (2006.01)
G06K 9/46 (2006.01)

(52) U.S. Cl.
CPC .......... *G06K 9/00624* (2013.01); *G06K 9/4642* (2013.01); *G06T 7/0012* (2013.01); *G06T 2207/10004* (2013.01); *G06T 2207/20148* (2013.01); *G06T 2207/30004* (2013.01)

(58) Field of Classification Search
CPC ....................................... G06K 9/40

USPC ................................... 382/254, 172
See application file for complete search history.

(56) References Cited

U.S. PATENT DOCUMENTS 4,731,863 A * 3/1988 Sezan et al. .................... 382/172
5,502,776 A * 3/1996 Manabe ........................ 382/172
(Continued)

FOREIGN PATENT DOCUMENTS

JP 2004-201730 7/2004
JP 2005-73817 3/2005
(Continued)

OTHER PUBLICATIONS

International Search Report in PCT/JP2013/072802.

*Primary Examiner* — Nirav G Patel
*Assistant Examiner* — Brian Shin
(74) *Attorney, Agent, or Firm* — Cooper & Dunham LLP

(57) ABSTRACT

In order to provide an image processing apparatus etc. that can precisely recognize multiple regions with density value fluctuation in an image with a simple operation in a process of recognizing a specific region from the image, a CPU performs threshold determination for a target pixel and the multiple pixels surrounding the target pixel (determination range) included in a three-dimensional original image by applying predetermined threshold conditions and specifies the target pixel as a recognized pixel when the threshold conditions are satisfied. The threshold conditions preferably apply different thresholds between a pixel on the same flat surface with the target pixel and a pixel on the other flat surface. By successively moving the target pixel (determination range) and repeating the above-mentioned threshold determination, it is performed also for the entire three-dimensional original image. This allows an operator to more precisely recognize a tissue with density value fluctuation such as a cartilage automatically without setting a starting point.

9 Claims, 12 Drawing Sheets

(56) References Cited

U.S. PATENT DOCUMENTS

| | | |
|---|---|---|
| 7,760,958 B2 * | 7/2010 | Sato et al. .................... 382/254 |
| 2002/0131643 A1 * | 9/2002 | Fels et al. .................... 382/224 |
| 2005/0063578 A1 | 3/2005 | Zhang et al. |
| 2005/0254697 A1 | 11/2005 | Zhang et al. |
| 2005/0259855 A1 | 11/2005 | Dehmeshki |
| 2006/0120585 A1 | 6/2006 | Zhang et al. |
| 2009/0116718 A1 | 5/2009 | Goto et al. |
| 2010/0208047 A1 * | 8/2010 | Kitamura ...................... 348/65 |
| 2010/0322496 A1 | 12/2010 | Liu et al. |
| 2012/0057754 A1 * | 3/2012 | Dunton et al. ................ 382/103 |

FOREIGN PATENT DOCUMENTS

| | | |
|---|---|---|
| JP | 2005-316583 | 11/2005 |
| JP | 2007-534352 | 11/2007 |
| JP | 2007-312838 | 12/2007 |
| JP | 2007-537812 | 12/2007 |
| JP | 2009-226043 | 10/2009 |
| JP | 2011-514190 | 5/2011 |
| WO | WO 2007/135913 | 11/2007 |

* cited by examiner

FIG.5
(a) 
(b) 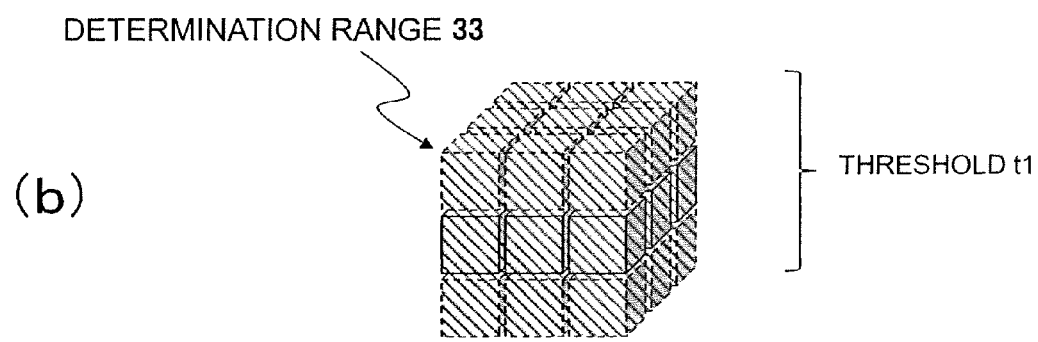
(c) 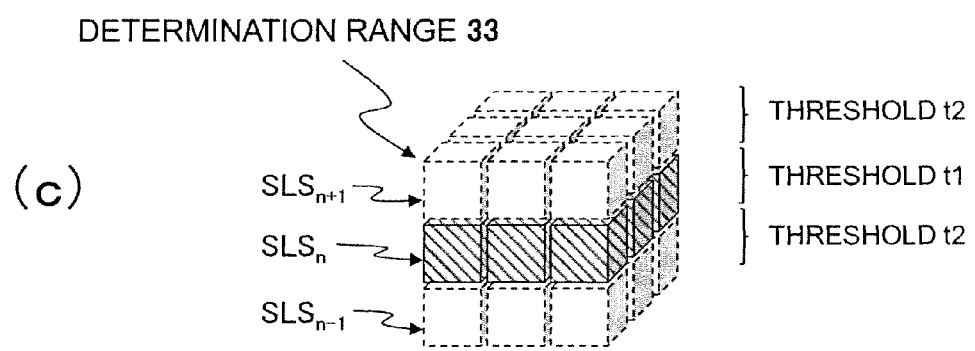

FIG.7
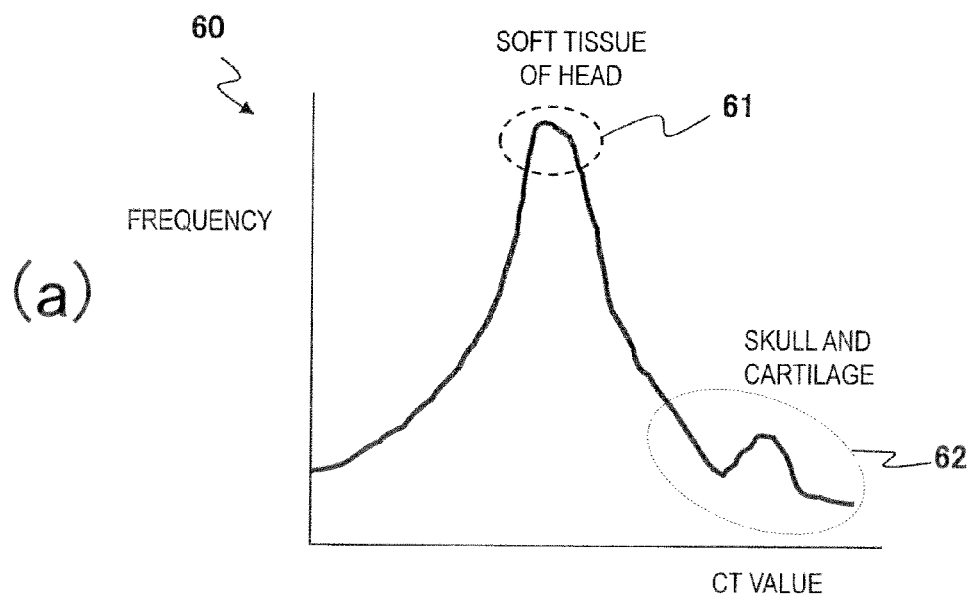
(a)
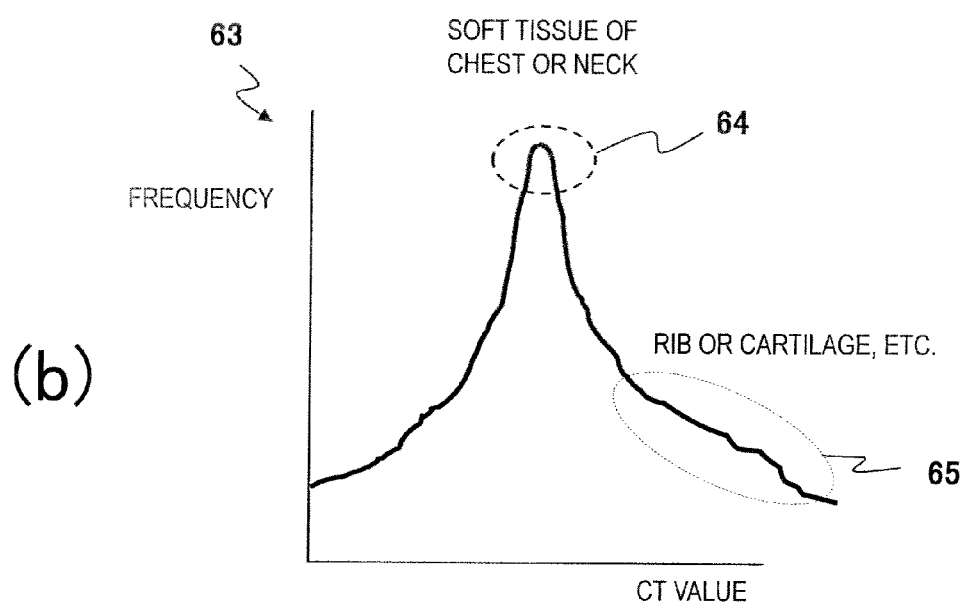
(b)

FIG.8
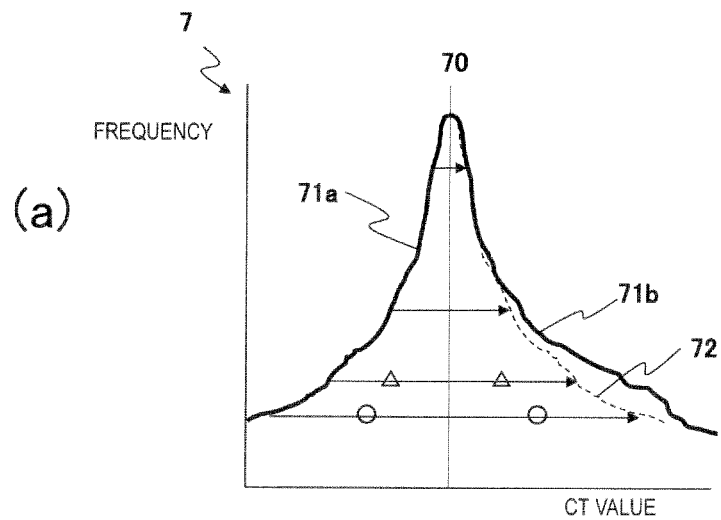
(a)
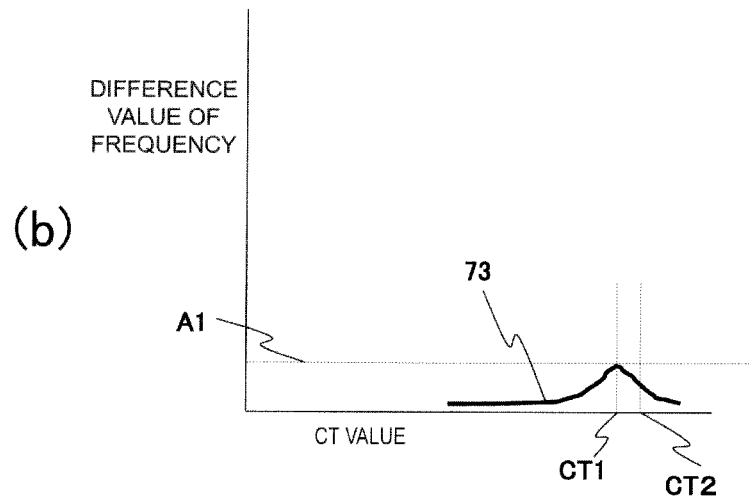
(b)

IMAGE PROCESSING APPARATUS AND IMAGE PROCESSING METHOD, CONFIGURED TO APPLY THRESHOLD CONDITIONS TO SPECIFY TARGET PIXEL

TECHNICAL FIELD

The present invention relates to an image processing apparatus etc. recognizing a specific region from an image.

BACKGROUND ART

Conventionally, a method has been known, in which a three-dimensional original image (three-dimensional volume data) is generated from a tomographic image group scanned by an X-ray CT (Computed Tomography) apparatus, an MRI (Magnetic Resonance Imaging) apparatus, etc. to generate an image appropriate for diagnosis (hereinafter, referred to as "diagnostic image") to display it after a specific tissue is extracted or eliminated from the three-dimensional original image. As the diagnostic image, for example, a three-dimensional volume rendering image, an MIP (Maximum Intensity Projection) image, etc. are created. Specifically, in case of observing blood vessel running in the head, a boning MIP image in which bone regions including a skull, cartilage, etc. were eliminated from the above tomographic image group may be generated.

By the way, in order to generate a diagnostic image in which a specific tissue was extracted or eliminated as described above, a method to automatically extract a certain organ region from an original image using a computer etc. is proposed. As the extraction method, for example, there is a region growing method etc. In the region growing method, a computer determines whether predetermined threshold conditions are satisfied for a pixel of a starting point or surrounding pixels including the pixel when an operator specifies the pixel of the starting point in an image and extends the pixels as an extraction region in a case where the conditions are satisfied.

In the patent literature 1, a method to prevent overextraction due to a few connected pixels when region extraction by the region growing method is performed is disclosed. This method extends a region only when pixels at a predetermined ratio satisfy conditions in sense regions which range to the extraction region and are comprised of multiple pixels. Also, in the patent literature 2, a method to distinguish tissues difficult to separate such as the cancellous bone, bone marrow, etc. which are internal tissues of a bone is disclosed. Specifically, it is described that a pixel value histogram of an MR image including the cancellous bone and bone marrow is created to calculate a cancellous bone volume fraction more precisely to separate the both by fitting with three normal distribution curves (values of the cancellous bone, the bone marrow, and the middle of the both).

CITATION LIST

Patent Literature

PTL 1: Japanese Patent No. 4538260
PTL 2: Japanese Patent No. 4487080

SUMMARY OF INVENTION

Technical Problem

However, even if the above region growing method and a tissue separation method were used, it was difficult to precisely distinguish and recognize a tissue with a large fluctuation of a density value such as a cartilage. Also, since all of the cartilage regions are not continuous but dotted in an image of the head, it was required for an operator to specify a starting point for each process in case of using the region growing method. Therefore, the operation is very complex.

The present invention was made in light of the above problems and has a purpose to provide an image processing apparatus and an image processing method which can precisely recognize multiple regions with a large fluctuation of a density value in an image with a simple operation in a process of recognizing a specific region from an image.

Solution to Problem

In order to achieve the above purpose, the first invention is an image processing apparatus executing a process of recognizing a specific region from an image, in which threshold determination is performed for a determination range including a target pixel and the surrounding multiple pixels from among pixels included in the image by applying predetermined threshold conditions, and the image processing apparatus is comprised of a threshold determination unit specifying the target pixel as a recognized pixel and a process execution unit executing the threshold determination repeatedly after moving the determination range successively in a case where the threshold conditions are satisfied by any pixel within the determination range.

Additionally, the above "recognizing" is to distinguish a corresponding pixel from the other pixels in a three-dimensional original image to retain it. The specific method, for example, is (a) to directly write a certain value as a mark in a former three-dimensional original image. Alternatively, it is (b) to record a recognized pixel as a binary image in a memory different from the three-dimensional original image.

The second invention is an image processing method to recognize a specific region from an image using a computer, in which threshold determination is performed by applying predetermined threshold conditions to a determination range including a target pixel and the surrounding multiple pixels from among pixels included in the image, and a threshold determination process of specifying the target pixel as a recognized pixel is executed repeatedly after moving the determination range successively in a case where the threshold conditions are satisfied by any pixel within the determination range.

Advantageous Effects of Invention

An image processing apparatus and an image processing method of the present invention can precisely recognize multiple regions with a large fluctuation of a density value in an image with a simple operation in a process of recognizing a specific region from an image. For example, an image process to eliminate the cartilage region can be performed more simply and precisely.

BRIEF DESCRIPTION OF DRAWINGS

FIG. 5 is a diagram describing how to apply threshold conditions in each processing mode: (a) is a single-pixel mode; (b) is an isotropic neighborhood determination mode; and (c) is an anisotropic neighborhood determination mode.

FIG. 7 is a diagram describing a density value histogram to be used in case of setting a threshold automatically.

FIG. 8(a) is a diagram describing the symmetrical distribution curve 72 using the left (a side of low CT values) data from a peak position of the density value histogram. FIG. 8(b) is the subtracted distribution value 73 for which a symmetrical distribution curve was subtracted from the original density value histogram.

DESCRIPTION OF EMBODIMENTS

Hereinafter, the embodiments of the present invention will be described in detail based on the diagrams.

First Embodiment

First, referring to FIG. 1, the configuration of the image processing system 1 applying the image processing apparatus 100 of the present invention will be described.

Figure 1:
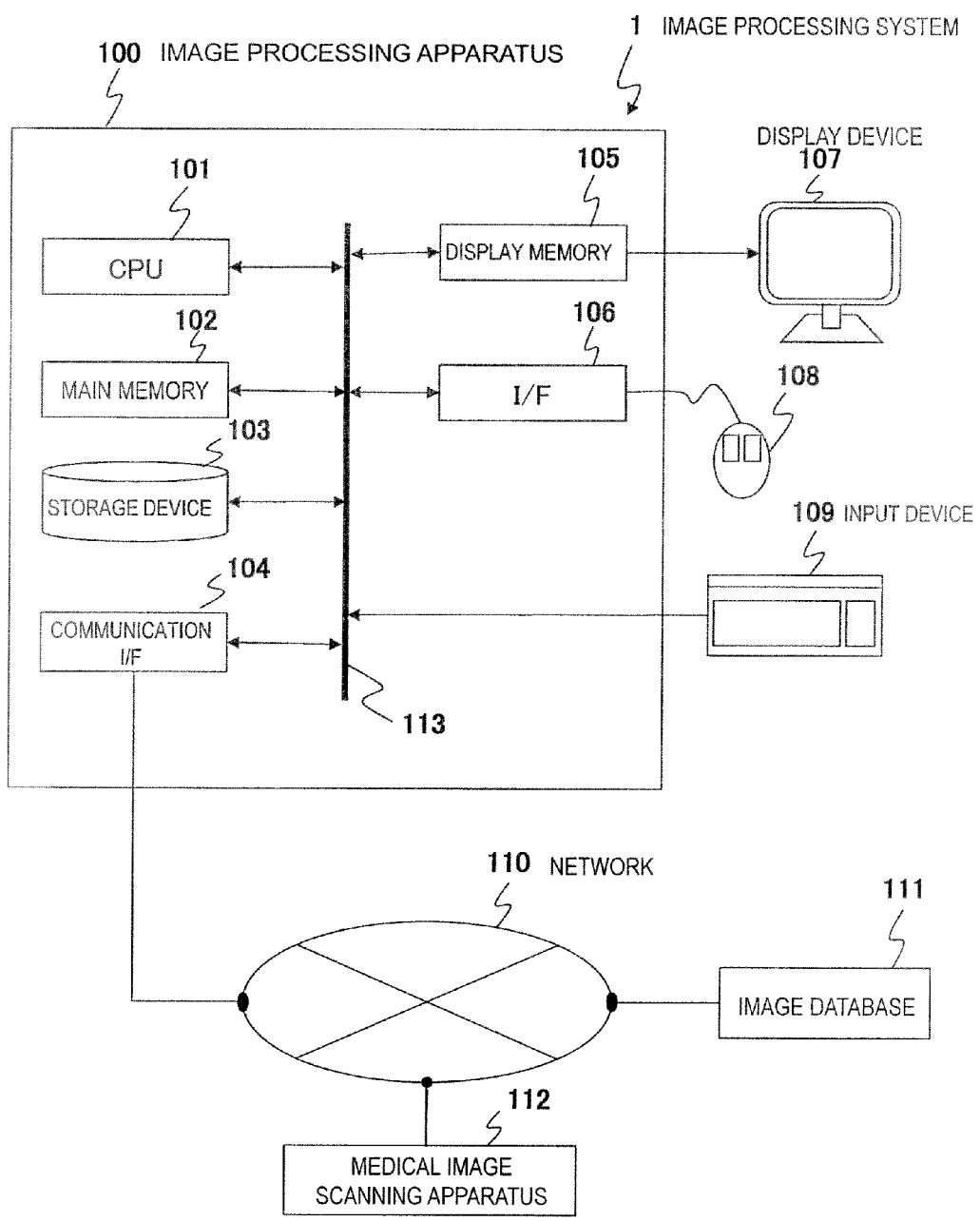
FIG. 1 is a diagram showing an overall configuration of the image processing apparatus 100.

As shown in FIG. 1, the image processing system 1 is comprised of the image processing apparatus 100 having the display device 107 and the input device 109, the image database 111 connected to the image processing apparatus 100 via the network 110, and the medical image scanning apparatus 112.

The image processing apparatus 100 is a computer performing processes such as image generation, image analysis, and so on. For example, the image processing apparatus 100 includes a medical image processing apparatus to be installed in a hospital etc.

The image processing apparatus 100, as shown in FIG. 1, is comprised of the CPU (Central Processing Unit) 101; the main memory 102; the storage device 103; the communication interface (communication I/F) 104; the display memory 105; and the interface (I/F) 106 to external equipment such as the mouse 108, and the respective parts are connected via the bus 113.

The CPU 101 executes a program stored in the main memory 102, the storage device 103, or the like by loading the program to a work memory region on the RAM of the main memory 102, controls driving of the respective parts connected via the bus 113, and achieves various processes performed by the image processing apparatus 100.

Also, the CPU 101 performs a process of recognizing a specific region from an image specified as a processing target in the diagnostic image generation process (refer to FIG. 3) to be described later. In the present embodiment, the image specified as a processing target is a three-dimensional original image composed of a plurality of stacked tomographic images. In the process of recognizing a region, the CPU 101 specifies a plurality of the surrounding pixels of a target pixel from among pixels included in the three-dimensional original image as a determination range and applies predetermined threshold conditions to the respective pixels in the determination range to perform threshold determination. Then, a target pixel becomes a recognized pixel when the threshold conditions are satisfied. Also, the CPU 101 performs the above threshold determination by scanning an entire three-dimensional original image. That is, by successively moving a determination range and repeating the above-mentioned threshold determination, it is performed for the entire three-dimensional original image.

Figure 2:
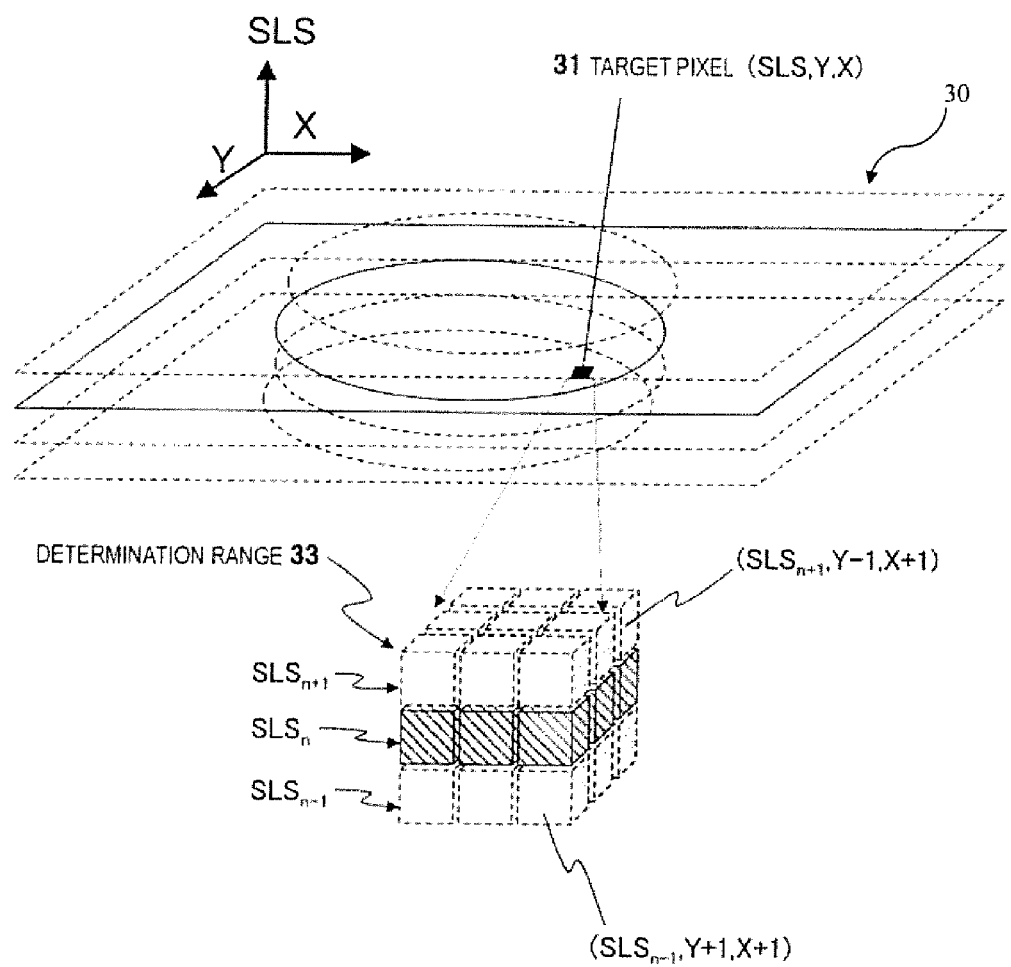
FIG. 2 is a diagram showing an example of a range (the determination range 33) to be specified as a threshold determination target that is the target pixel 31 and the surrounding pixels of the target pixel 31 within the three-dimensional original image 30 to be specified as a processing target.

At this point, "a plurality of the surrounding pixels of a target pixel (determination range)" specified as a target of threshold determination are pixels within a predetermined distance range in the X, Y, and slice (SLS) directions with the target pixel 31 included in the three-dimensional original image 30 centered as shown in FIG. 2. That is, they are pixels located in the vicinity of the target pixel 31. In the present invention, the target pixel 31 specified as a target of threshold determination and a plurality of the surrounding pixels are referred to as the determination range 33. For example, the determination range 33 is the pixel group of 3×3×3 in the slice (SLS), horizontal (X), and depth (Y) directions from the target pixel 31 that is centered. Additionally, an extent of the determination range 33 is not limited to this, but the determination range may be further extended to the pixel group of 5×3×3 etc.

The details for how to perform threshold determination and threshold setting will be described later.

The main memory 102 is comprised of an ROM (Read Only Memory), an RAM (Random Access Memory), and so on. The ROM holds a boot program of a computer, a program such as BIOS, data, and so on permanently. Also, the RAM holds a program, data, and so on loaded from the ROM, the storage device 103, etc. temporarily as well as includes a work memory region used for various processes performed by the CPU 101.

The storage device 103 is a storage device for reading and writing data to an HDD (Hard Disk Drive) and the other recording media as well as stores a program to be performed by the CPU 101, data required to execute the program, an OS (Operating System), and so on. As the program, a control program equivalent to an OS and an application program are stored. These respective program codes are read out by the CPU 101 as needed and are moved to an RAM of the main memory 102 to operate as various execution units.

The communication I/F 104 has a communication control device and a communication port and mediates communication between the image processing apparatus 100 and the network 110. Also, the communication I/F 104 performs communication control to the image database 111, other computers, an X-ray CT apparatus, and the medical image scanning apparatus 112 such as an MRI apparatus via the network 110.

The I/F 106 is a port to connect peripheral devices and transmits/receives data with the peripheral devices. For example, it may be configured so that a pointing device such as the mouse 108 and a stylus pen is connected via the I/F 108.

The display memory 105 is a buffer accumulating display data to be input from the CPU 101 temporarily. The accumulated display data is output to the display device 107 at a predetermined timing.

The display device 107 is comprised of a liquid-crystal panel, a display device such as a CRT monitor, and a logic circuit to execute a display process in conjunction with the display device and is connected to the CPU 101 via the display memory 105. The display device 107 displays display data accumulated in the display memory 105 by control of the CPU 101.

The input device 109 is, for example, an input device such as a keyboard and outputs various commands and information input by an operator to the CPU 101. An operator operates the image processing apparatus 100 interactively using an external device such as the display device 107, the input device 109, and the mouse 108.

The network 110 includes various communication networks such as a LAN (Local Area Network), a WAN (Wide Area Network), the Intranet, and the Internet and mediates communication connection between the image database 111, a server, the other information devices, etc. and the image processing apparatus 100.

The image database 111 is to accumulate and memorize image data scanned by the medical image scanning apparatus 112. Although the image processing system 1 shown in FIG. 1 has a configuration where the image database 111 is connected to the image processing apparatus 100 via the network 110, it may be configured so that the image database 111 is provided in, for example, the storage device 103 inside the image processing apparatus 100.

Next, referring to FIGS. 3 to 8, operations of the image processing apparatus 100 will be described.

Figure 3:
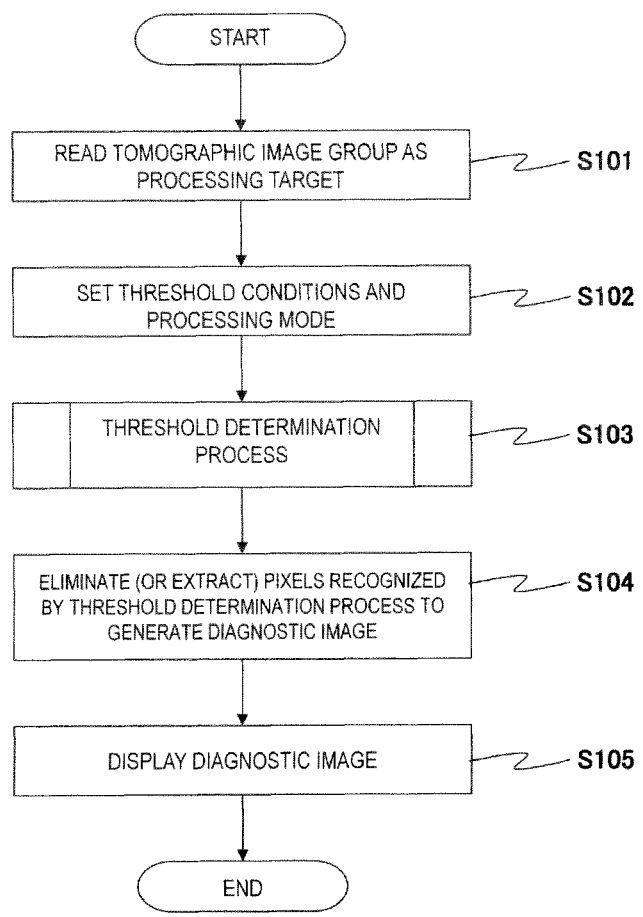
FIG. 3 is a flow chart describing a flow of a diagnostic image generation process that the image processing apparatus 100 related to the present invention executes.

The CPU 101 of the image processing apparatus 100 reads out a program and data for diagnostic image generation of FIG. 3 from the main memory 102 or the storage device 103 and executes a process based on the program and the data.

Additionally, when a diagnostic image generation process starts, image data specified as a processing target is loaded from the image database 111 via the network 110 and the communication I/F 104 and is memorized in the storage device 103 of the image processing apparatus 100.

The image data specified as a processing target is, for example, a three-dimensional original image in which multiple tomographic images including a target region are stacked. For example, as shown in FIG. 2, the three-dimensional original image 30 that is comprised of tomographic images of multiple slices $SLS_{n-2}$, $SLS_{n-1}$, $SLS_n$, $SLS_{n+1}$ . . . is read as the processing target image data. Also, as an example of ideal image data, a CT image, an MR image, and so on can be considered. The purpose of the present embodiment is to finally generate an MIP image (diagnostic image) in which bones and cartilages were eliminated properly while calcified regions of blood vessels are left. Therefore, the three-dimensional original image 30 specified as a processing target is an image of the head, but the application range of the present invention is not limited to the head image. For example, the present invention can be applied also to cases where the cancellous bone that is an internal tissue of a bone is distinguished from the bone marrow in a cross-sectional image of the bone and where a rib with density value fluctuation is distinguished in a chest image.

The CPU 101 reads a tomographic image group (a three-dimensional original image) specified as a processing target from among the read image data (Step S101).

Next, the CPU 101 sets a method for deciding threshold conditions and a processing mode of a threshold determination process (Step S102). In Step S102, the CPU 101 displays the operation window 20 as shown in FIG. 4 for example on the display device 107 and receives various settings and input operations by an operator.

Figure 4:
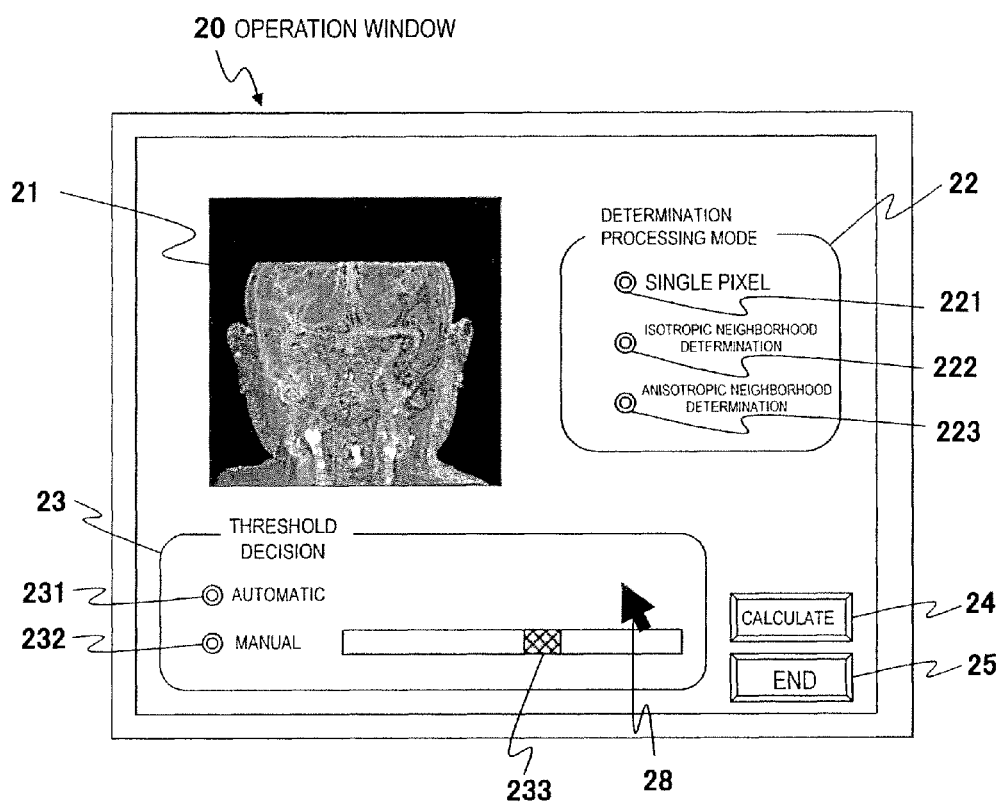
FIG. 4 is an example of the operation window 20.

As shown in FIG. 4, the operation window 20 is provided with various buttons such as the image display area 21, the determination processing mode selection field 22, the threshold decision field 23, the calculation button 24, and the end button 25.

The image display area 21 displays the entire or a part of the three-dimensional original image 30 specified as a processing target, a diagnostic image generated as a processing result, and so on.

The determination processing mode selection field 22 is a field to select a processing method (processing mode) for threshold determination and is provided with the respective radio buttons 221, 222, and 223 of a single-pixel mode, an isotropic neighborhood determination mode, and an anisotropic neighborhood determination mode.

The single-pixel mode is a processing mode to perform threshold determination for a target pixel itself. Similarly to a conventional and general threshold process, a threshold process is performed only for the target pixel at a predetermined threshold.

The isotropic neighborhood determination mode is a mode to perform threshold determination for a target pixel and the surrounding pixels using the same threshold conditions.

The anisotropic neighborhood determination mode is a mode to perform threshold determination for pixels on a flat surface including a target pixel and pixels on the other flat surface using different threshold conditions.

FIG. 5 is a diagram describing a determination range and differences between threshold conditions to be applied in each processing mode.

As shown in FIG. 5(a), in the single-pixel mode, only the target pixel 31 is specified as the determination range. Also, as a threshold, the same thresholds t1 are used for each target pixel. The CPU 101 determines the target pixel 31 in thresholds t1, and the target pixel 31 is specified as a recognized pixel when the conditions are satisfied.

Also, as shown in FIG. 5(b), in an isotropic neighborhood determination mode, a pixel range (ex: 3×3×3) in which the target pixel 31 is centered is specified as the determination range 33 to determine all the respective pixels included in the determination range 33 in thresholds t1. Then, the target pixel 31 is specified as a recognized pixel when any pixel within the determination range 33 satisfies the above threshold conditions (t1). By including the surrounding pixels in the determination range 33, a tissue with density value fluctuation such as a cartilage is easy to be extracted.

Also, as shown in FIG. 5(c), in an anisotropic neighborhood determination mode, a pixel range (ex: 3×3×3) in which the target pixel 31 is centered is specified as the determination range 33, thresholds t1 are applied to a flat surface (slice $SLS_n$) including the target pixel 31, and then different thresholds t2 are applied to the other flat surfaces (slices $SLS_{n-1}$, $SLS_{n+1}$) to perform threshold determination. Then, the target pixel 31 is specified as a recognized pixel when any pixel satisfies the above threshold conditions. By including the surrounding pixels in the determination range and setting different thresholds between the flat surface including the target pixel and the other flat surfaces, which can widen the threshold conditions, and a tissue with density value fluctuation is further easy to be extracted. Hence, cartilages can be recognized more precisely.

The description of FIG. 4 will be performed again.

The threshold decision field 23 of the operation window 20 is provided with the threshold automatic setting radio button 231 to be operated in case of automatically setting a threshold, the threshold manual setting radio button 232 to be operated in case of manually setting a threshold, and the slider 233 to change a threshold when manually setting the threshold. The slider 233 is moved by the mouse pointer 28. The threshold setting will be described later.

The calculation button 24 is a button to be operated in case of starting a threshold determination process. When the calculation button 24 is pressed down, the CPU 101 starts the threshold determination process in a processing mode set in the determination processing mode selection field 22 and under threshold conditions determined in the threshold decision field 23.

The end button 25 is a button to be operated when the operation window 20 is closed to end a diagnostic image generating process.

In the operation window 20, when a threshold decision method and a processing mode are selected (Step S102 of FIG. 3), the CPU 101 sets the determination range 33 according to the processing mode. Then, the CPU 101 executes a threshold determination process according to the selected threshold decision method and processing mode (Step S103). The threshold determination process will be described in detail later.

The CPU 101 eliminates or extracts pixels recognized by the threshold determination process of Step S103 to generate a diagnostic image (Step S104). For example, an MIP image in which bones were eliminated from a three-dimensional original image, a three-dimensional volume rendering image, etc. are general as a diagnostic image for blood vessel observation. The CPU 101 saves generated diagnostic images in the storage device 103 as well as displays them on the display device 107 (Step S105) to end the process.

Next, referring to FIG. 6, the threshold determination process in Step S103 will be described.

The threshold determination process is performed using any of the three modes: a single-pixel mode; an isotropic neighborhood determination mode; and an anisotropic neighborhood determination mode as described above.

In the present embodiment, it is desirable that an anisotropic neighborhood determination mode is selected and that a threshold is automatically set as a most desirable setting example to generate a diagnostic image (MIP image) in which bones and cartilages were eliminated in order to draw a blood vessel image of the head.

Figure 6:
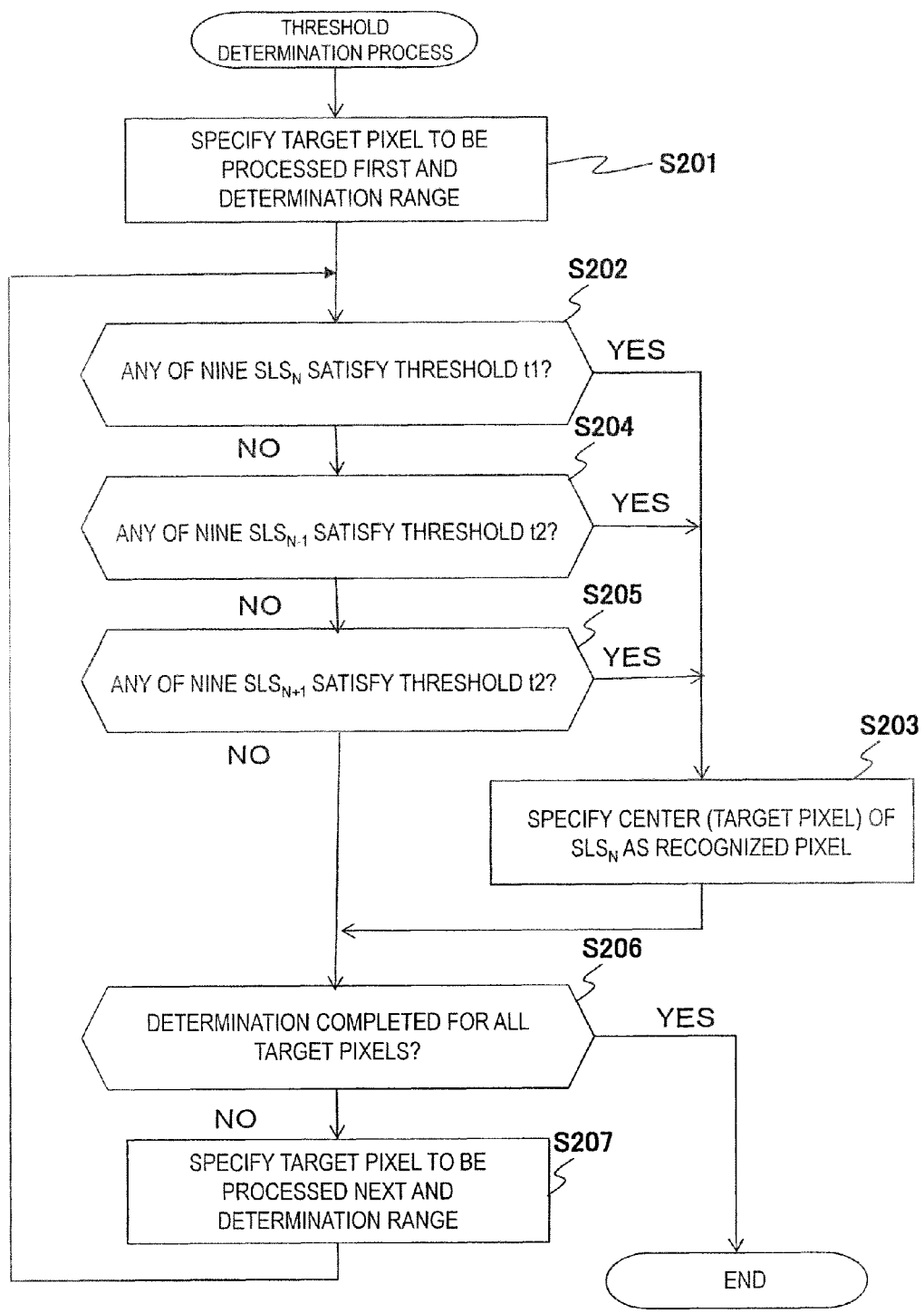
FIG. 6 is a flow chart describing a flow of a threshold determination process by the isotropic neighborhood determination mode.

FIG. 6 is a flow chart describing a flow of a threshold determination process by an isotropic neighborhood determination mode. Also, the first threshold t1 and the second threshold t2 to be used for threshold determination are manually set in advance or are calculated automatically. The threshold automatic setting method will be described later.

As shown in FIG. 6, first, the CPU 101 specifies the target pixel 31 and the determination range 33 to be processed first (Step S201). The target pixel 31 etc. to be processed first is not specified by an operator in the same manner as a region growing method etc., but is decided by the CPU 101. For example, the CPU 101 moves and scans the determination range 33 from an end point of the three-dimensional original image 30 in turn to perform threshold determination for the entire three-dimensional original image 30 eventually. In the following description, as an example, an image group (3×3×3=27 pixels) in which one pixel was added in the respective slice SLS, Y, and X directions from the target pixel 31 that is centered is specified as the determination range 33.

In an anisotropic neighborhood determination mode, the CPU 101 first determines whether any of nine pixels in a slice SLS, including the target pixel 31 satisfies the first threshold t1 or not (Step S202). If any of nine pixels in the slice $SLS_n$ including the target pixel 31 satisfies the first threshold t1 (Step S202: Yes), the center point in the slice $SLS_n$, i.e. the target pixel 31 is specified as a recognized pixel (Step S203). If any of nine pixels in a flat surface (slice $SLS_n$) including the target pixel 31 does not satisfy the first threshold t1 (Step S202: No), whether any of nine pixels on the other flat surface (slice $SLS_{n-1}$) satisfies the second threshold t2 or not is determined (Step S204).

If any of nine pixels in the slice $SLS_{n-1}$, satisfies the second threshold t2 (Step S204: Yes), the center point in the slice $SLS_n$, i.e. the target pixel 31 is specified as a recognized pixel (Step S203). If any of nine pixels in the slice $SLS_{n-1}$ does not satisfy the second threshold t2 (Step S204: No), whether any of nine pixels on the other flat surface (slice $SLS_{n+1}$) satisfies the second threshold t2 or not is determined (Step S205). If any of nine pixels in slice $SLS_{n+1}$ satisfies the second threshold t2 (Step S205: Yes), the center point in the slice $SLS_n$, i.e. the target pixel 31 is specified as a recognized pixel (Step S203). If any of nine pixels in the slice $SLS_{n+1}$ does not satisfy the second threshold t2 (Step S205: No), the target pixel 31 is not specified as a recognized pixel, but the next determination range 33 will be processed.

That is, the CPU 101 determines whether threshold determination has completed for all the pixels of the three-dimensional original image 30 or not (Step S206), and if the threshold determination has not completed (Step S206: No), the CPU 101 moves the determination range 33 to the next by one pixel or the number of predetermined pixels (Step S207).

The CPU 101 repeats threshold determination by the first threshold t1 and the second threshold t2 for the next determination range 33 (Step S202 to Step S205). That is, if any pixel satisfies threshold conditions after applying the first threshold t1 to a flat surface including the center pixel (the target pixel 31) of the next determination range 33 and applying the second threshold t2 to the other flat surface, the target pixel 31 is specified as a recognized pixel.

When threshold determination completes for all the pixels of the three-dimensional original image 30 (Step S206: Yes), the threshold determination process ends.

Additionally, in the above process, there are, for example, the following (a) and (b) methods as a method to keep a recognized pixel, and either method may be used.

(a) A specific value is directly written as a mark in a three-dimensional original image.

(b) A recognized pixel is recorded as a binary image in another memory different from a three-dimensional original image.

Also, it may be configured so that the above threshold determination process is executed for pixels to be used for generating a diagnostic image to recognize or not to recognize each pixel while the diagnostic image (MIP image) is being calculated. In this case, the threshold determination process may not be performed for unnecessary pixels to generate a diagnostic image.

Although the threshold determination process described above is that for an anisotropic neighborhood determination mode, in an isotropic neighborhood determination mode, the same threshold t1 is applied to all the pixels in the determination range 33 (for example, a pixel of 3×3×3 with a target pixel centered) to specify the target pixel 31 as a recognized pixel if any pixel satisfies the threshold t1. The threshold determination is repeatedly executed over the entire image while the determination range 33 is being moved.

Next, a method for setting a threshold automatically will be described, referring to FIGS. 7 and 8. FIG. 7(a) is a diagram schematically showing the histogram 60 of density values (CT values) in a CT image of the head, and FIG. 7(b) is a diagram schematically showing the histogram 63 of density values (CT values) in a CT image of the chest.

As shown in FIG. 7(a), the density value histogram 60 of the head has a characteristic in which the peak 61 showing a head soft tissue and the small peak 62 corresponding to the skull and cartilages appear. The CPU 101 can automatically decide a threshold of a bone region based on position information (CT value range) of the small peak 62 corresponding to the skull and cartilages.

On the other hand, as shown in FIG. 7(b), although the peak 64 showing soft tissues of the chest or the neck appears in the density value histogram 63 of the chest, an apparent peak showing CT values of ribs and cartilages (the broken line 65 in FIG. 7(b)) does not appear. Thus, if characteristics of sites (ribs and cartilages) to be distinguished do not appear, a threshold t1 (threshold t2) is decided using a method shown in FIG. 8.

That is, the CPU 101 first calculates the histogram 7 of a CT image as shown in FIG. 8(a). A peak (the peak 70) of the calculated histogram 7 and a CT value in the peak position (the peak 70) are calculated. Of the distribution curves in the histogram 7, one distribution curve whose CT value is lower than the peak 70 is referred to as 71a, and the other distribution curve whose CT value is higher than the peak 70 is referred to as 71b.

Additionally, although FIG. 8(a) is an example where there is one distribution peak, a plurality of peaks may appear. In this case, for example, a peak whose CT value is the highest among peak positions can be used when a bone threshold is calculated.

Next, the CPU 101 calculates the distribution curve 72 symmetrical to the distribution curve 71a on the lower side of CT values with the peak 70 being a boundary position on the higher side of CT values and specifies the symmetrical distribution curves 71a and 72. Then, the symmetrical distribution curves 71a and 72 are subtracted from the distribution curves 71a and 71b of the original histogram 7 to calculate the subtracted distribution curve 73. FIG. 8(b) shows an example of the subtracted distribution curve 73.

The horizontal axis and the vertical axis of the distribution curve shown in FIG. 8(b) are respectively a CT value and a differential value of frequency.

The CPU 101 calculates a threshold based on the subtracted distribution curve 73.

For example, a peak position CT1 of the subtracted distribution curve 73 and a differential value A1 at the peak position CT1 shown in FIG. 8(b) are calculated to specify a higher CT value (CT2) from among CT values whose differential value is A1/N as the first threshold t1. In this case, N is a predetermined constant. Also, a threshold t1 may be calculated as f(expCT) using an expected value expCT of the subtracted distribution curve 73. Additionally, f( ) shows an arbitrary function, and the expected value expCT should be calculated using the following formula for example.

[Number 1]

$$\mathrm{expCT} = \frac{\sum_i F_i \cdot CT_i}{\sum_i F_i} \quad (1)$$

In the formula, i is an index showing a class of a CT value, $CT_i$ is a CT value (each value of the horizontal axis in FIG. 8(b)) corresponding to an index i, and $F_i$ is a frequency (each value of the vertical axis in FIG. 8(b)) corresponding to an index i.

Also, the second threshold t2 may be calculated as the following formula (2).

$$t2 = t1 - B \quad (2)$$

In the formula, B should be a value included a fluctuation range (approx. 30 to 50) of a cartilage density value.

Figure 9:
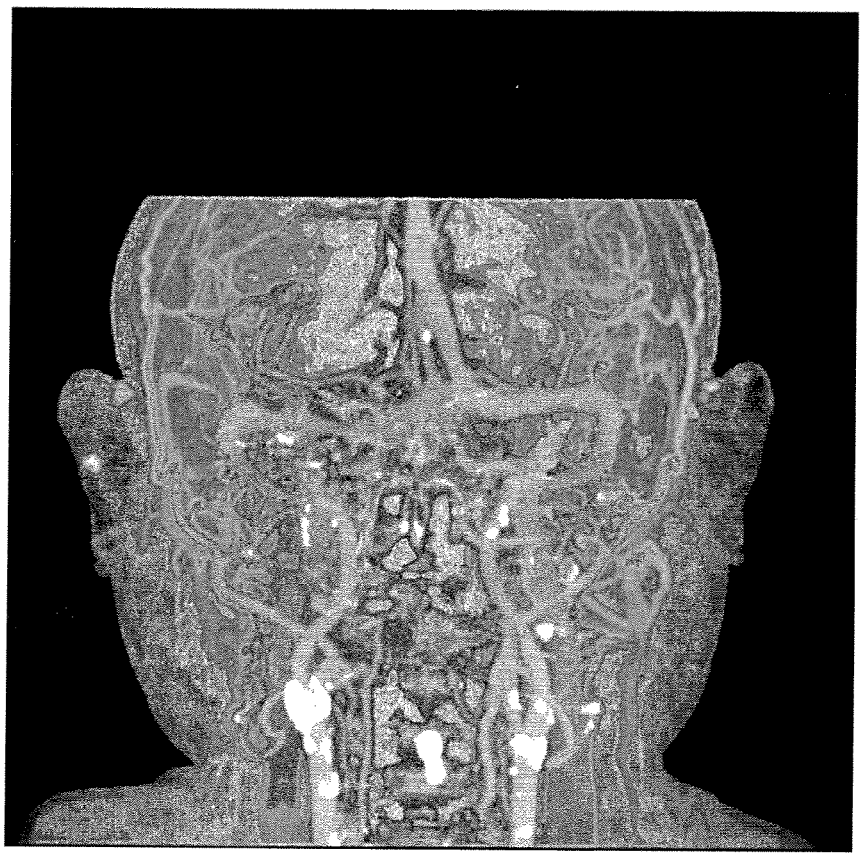
FIG. 9 is a boning MIP image of the head which was generated by eliminating recognized pixels after performing threshold determination using the anisotropic neighborhood determination mode and the threshold automatic setting.

FIG. 9 shows a threshold set automatically by the method of FIG. 8 and an MIP image in which bones were eliminated by a threshold determination process in an anisotropic neighborhood determination mode. The difference between a threshold t2 and a threshold t1 is 50 (t2=t1−50).

Figure 10:
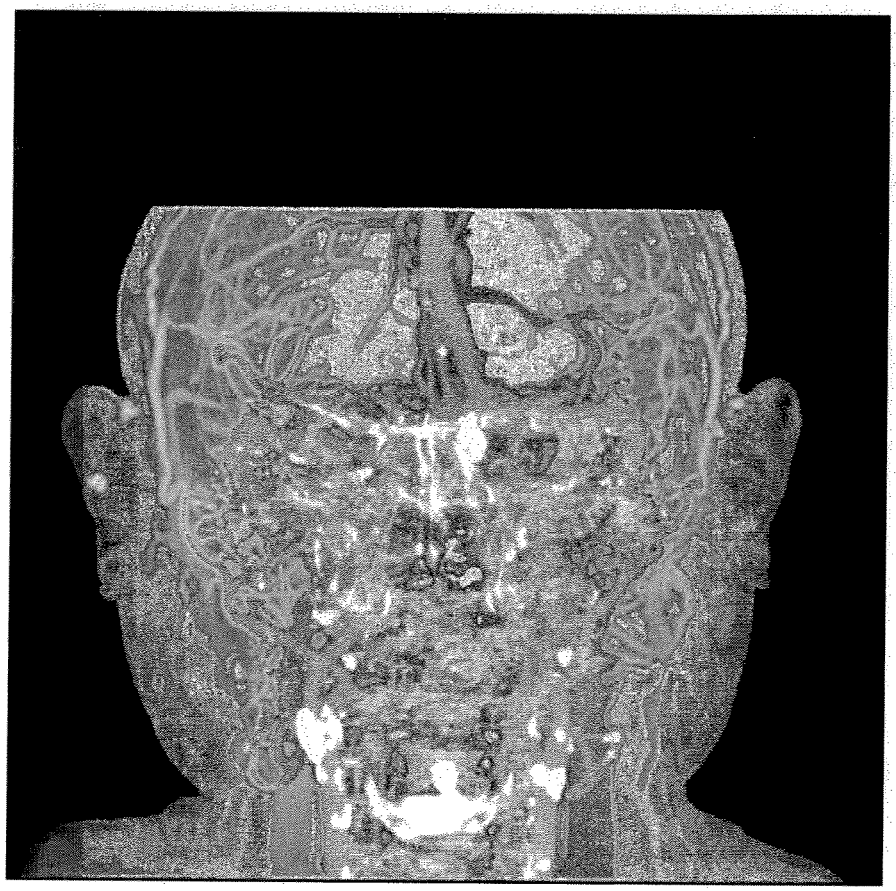
FIG. 10 is an MIP image of the head whose bones were eliminated using a conventional method (a pixel single-pixel mode and threshold manual setting).

As a comparative example, FIG. 10 shows a bone-eliminated MIP image obtained in a case where a threshold determination process were performed by threshold manual setting in a single-pixel mode.

Compared to the image shown in FIG. 10, it is easy to observe blood vessel running in the image shown in FIG. 9 because particularly cartilages around the nose in the center of the image were eliminated. Also, calcified regions of blood vessels (parts whose density value of the image is high (white)) remain.

Additionally, when manually setting a threshold, an operator selects the threshold manual setting radio button 232 in the threshold decision field 23 in the operation window 20 shown in FIG. 4 and operates the slider 23 for threshold setting to set a threshold accordingly.

As described above, according to the image processing apparatus 100 related to the present invention, the CPU 101 applies predetermined threshold conditions to multiple pixels (the determination range 33) surrounding the target pixel 31 included in the three-dimensional original image 30 comprised of a plurality of stacked tomographic images to perform threshold determination and specifies a target pixel as a recognized image in a case where the threshold conditions are satisfied. Also the CPU 101 does not grow a region from the starting point specified by an operator like a conventional region growing method, but repeatedly executes the above threshold determination by moving the target pixel to the other pixel sequentially to perform the threshold determination for the entire three-dimensional original image 30.

Hence, a tissue with density value fluctuation (fluctuation range) such as a cartilage can be recognized more precisely. Additionally, because a threshold determination process is performed by scanning the entire image, it is unnecessary to specify a starting point. In case of using the conventional region growing method, although it is necessary for an operator to specify a starting point for each region in order to extract (recognize) dispersed regions, it is unnecessary to specify the starting point by applying the present invention, which results in easy operation.

Also, if the threshold determination process applies a different threshold between a pixel on the same flat surface with the target pixel 31 and a pixel on the other flat surface in the determination range 33 and determines that threshold conditions are satisfied by any pixel in the determination range 33, the target pixel 31 is specified as a recognized pixel (anisotropic neighborhood determination mode). Hence, the threshold conditions can be widened, which can precisely recognize a tissue with density value fluctuation such as, in particular, cartilages of the head, internal tissues of a bone, and ribs.

Also, if the threshold determination process applies the same threshold to a target pixel and the surrounding multiple pixels (the respective pixels within the determination range 33) and determines that threshold conditions are satisfied by any pixel, the target pixel 31 may be specified as a recognized pixel (isotropic neighborhood determination mode). Hence, because a target pixel can be determined as a recognized pixel when nearby pixels satisfy threshold conditions even if the target pixel 31 itself does not satisfy the threshold conditions, it is suitable to recognize a tissue with density value fluctuation.

Also, it is desirable to calculate threshold conditions based on a density value histogram of the three-dimensional original image 30. This can set a threshold appropriate for characteristics of density value distribution of the original image, which can obtain a more precise result.

Also, threshold conditions may be calculated based on characteristics of the subtracted distribution curve 73 by calculating a peak position (the peak 70) of a density value histogram (71a and 71b) of the subtracted distribution curve 73, calculating the distribution curve 72 symmetrical at a peak position using data (the distribution curve 71a) of a part whose density value is lower than the peak position (the peak 70), and subtracting symmetrical distribution curves 71a and 72 from the distribution curves 71a and 71b of the original histogram to calculate the subtracted distribution curve 73.

Hence, a suitable threshold can be set automatically even from a histogram that does not have a characteristic distribution shape showing a tissue to be recognized such as a chest image, for example.

Also, in order to allow an operator to set threshold conditions, for example, it is desirable to further have a GUI (Graphical User Interface) such as the slider 233 that changes a threshold on the operation window 20.

Also, it is desirable to provide the determination processing mode selection field 22 selecting "single-pixel mode": performing threshold determination for a single target pixel, "isotropic neighborhood determination mode": performing threshold determination for a target pixel and the surrounding pixels using the same threshold conditions, or "anisotropic neighborhood determination mode": performing threshold determination for a flat surface including a target pixel and the other flat surface using different threshold conditions as a processing mode of the threshold determination on the operation window 20. Hence, a threshold determination process can be executed by switching a processing mode easily.

Also, it is desirable to provide the threshold decision field 23 selecting whether to allow an operator to manually set threshold conditions or whether to set them automatically on the operation window 20. Hence, a threshold determination process can be executed by switching a threshold setting method easily.

Also, it is desirable to generate diagnostic images such as a three-dimensional original image and an MIP image by eliminating or extracting a recognized pixel recognized in the above threshold determination process from the three-dimensional original image 30. Hence the present invention can be used for generating diagnostic images. For example, for observing blood vessel running, a suitable MIP image in which the skull and cartilages were eliminated properly can be generated.

Additionally, although an example where an anisotropic neighborhood determination mode was set as a processing mode with an automatically set threshold was described in the above first embodiment, the settings are not limited to this combination. For example, a threshold may be manually set in an anisotropic neighborhood determination mode. Also, a threshold may be automatically or manually set in an isotropic neighborhood determination mode.

Figure 11:
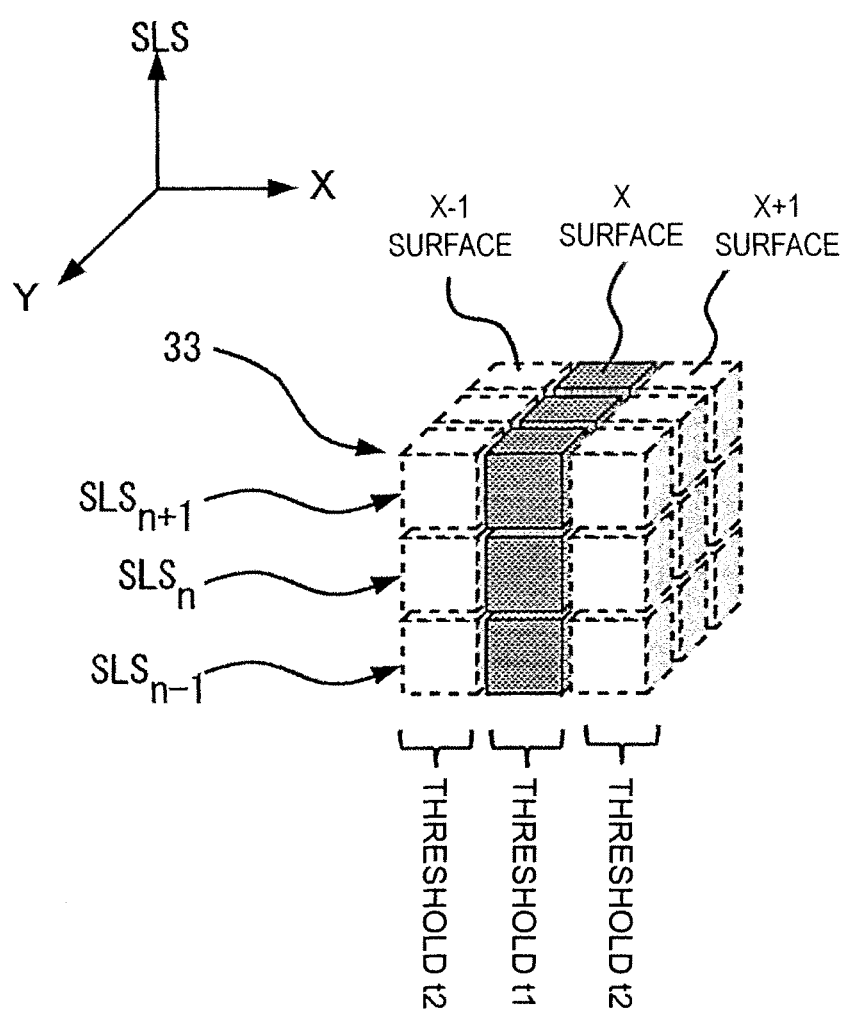
FIG. 11 is another example of threshold condition setting in the anisotropic neighborhood determination mode.

Also, although an example where a different threshold is applied to a slice direction in the anisotropic neighborhood determination mode was shown in the above description, the application is not limited to this example. For example, as shown in FIG. 11, a different threshold (the first threshold t1 or the second threshold t2) may be applied to the X direction. That is, a threshold t1 may be applied to a Y-SLS flat surface (X=X) including a target pixel, and a threshold t2 may be applied to the next Y-SLS flat surface (a surface of X=X−1 and a surface of X=X+1). Similarly, a different threshold may be applied to the Y direction.

Also, although it was described that a diagnostic image (MIP image) was generated after a region was recognized (extracted/eliminated) by threshold determination in the above description, a temporal order between a threshold determination timing and a diagnostic image generation timing is not always limited to this order. A diagnostic image may be generated by utilizing or ignoring a recognized pixel while the above threshold determination process is being performed at the same time when calculation for the diagnostic image is performed.

Second Embodiment

Next, referring to FIG. 12, the second embodiment will be described. For the image processing apparatus 100 related to the second embodiment, different threshold conditions are set according to a distance from a target pixel in case of widening a determination range in an anisotropic neighborhood determination mode.

Additionally, because the hardware configuration of the image processing apparatus 100 of the second embodiment is similar to the first embodiment, the same descriptions will be omitted, and the same symbols will be used to describe the same parts.

Figure 12:
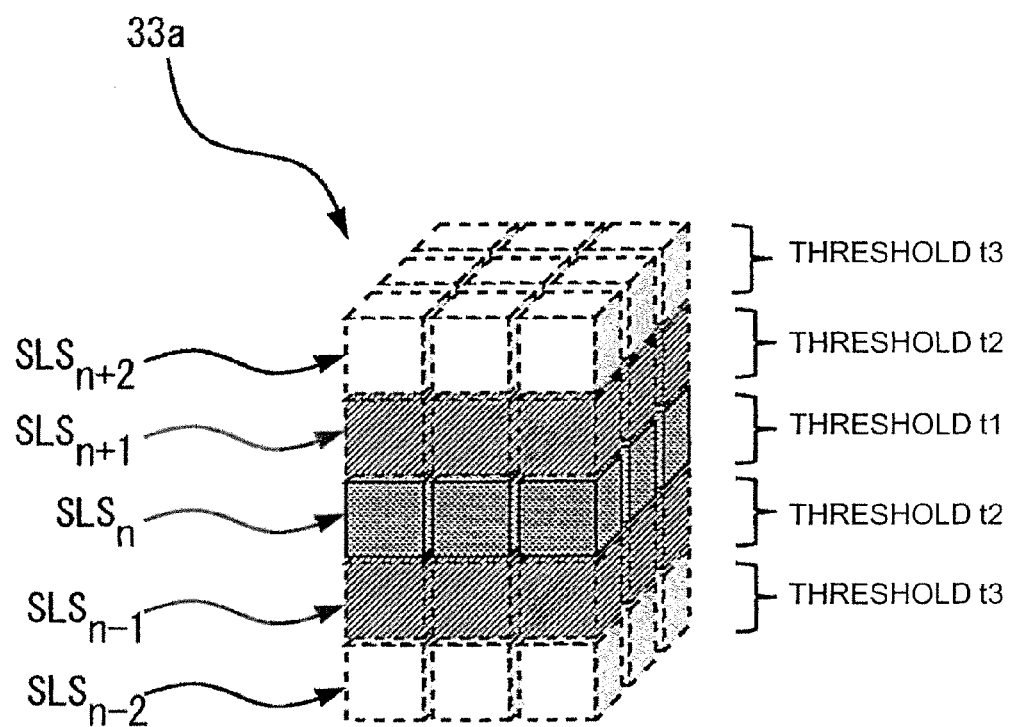
FIG. 12 is an example of setting threshold conditions different according to a distance from a target pixel in the anisotropic neighborhood determination mode.

That is, in the second embodiment, the CPU 101 sets a relatively wide determination range around a target pixel like the determination range 33a shown in FIG. 12 in a threshold determination process. Then, the first threshold t1 is applied to a flat surface $SLS_n$ including a target pixel, the second threshold t2 is applied to flat surfaces $SLS_{n-1}$ and $SLS_{n+1}$ adjacent by one pixel, and then the third threshold t3 is applied to flat surfaces $SLS_{n-2}$ and $SLS_{n+2}$ adjacent by two pixels. Then, the CPU 101 specifies a target pixel as a recognized pixel when the CPU 101 determines that threshold conditions are satisfied in any pixel within the determination range 33a.

In case of setting a threshold automatically, similarly to the first embodiment, a CT-value range of a tissue to be recognized based on a density value histogram of the three-dimensional original image 30 is decided to set a threshold t1. Also, another threshold t2 is calculated using the above formula (2) (t2=t1−B), and a threshold t3 should be calculated using the following formula (3).

$$t3 = t1 - C \quad (3)$$

In this formula, C is a different value from B. For example, in order to recognize a cartilage, the value falls within a fluctuation range (approx. 30 to 50) of the cartilage density value.

As described above, the image processing apparatus 100 of the second embodiment sets different threshold conditions according to a distance from a target pixel in an anisotropic neighborhood determination mode and specifies the target pixel as a recognized pixel when the threshold conditions are satisfied in any pixel in the determination range 33a.

Hence, a tissue whose fluctuation range of a density value is large and the distribution is complicated can be recognized more precisely.

Additionally, although three thresholds t1, t2, and t3 are to be set in an example of FIG. 12, in case of further widening a determination range, more threshold conditions are set, and the threshold conditions should be changed gradually according to a distance from a target pixel. An application range of a threshold is also not limited to one pixel, and different thresholds may be applied by a certain width (the number of pixels).

Referring to the attached diagrams, although suitable embodiments of an image processing apparatus related to the present invention were described above, the present invention is not limited to such embodiments. It is obvious that a person skilled in the art can conceive various changes or modifications within the scope of the technical idea disclosed in the present application, and it is understood that they naturally belong to the technical scope of the present invention.

DESCRIPTION OF REFERENCE NUMERALS

1: image processing system, 100: image processing apparatus, 101: CPU, 102: main memory, 103: storage device, 104: communication I/F, 105: display memory, 106: I/F, 107: display device, 108: mouse, 109: input device, 110: network, 111: image database, 112: medical image scanning apparatus, 113: bus, 20: operation window, 21: image display area, 22: determination processing mode selection field, 23: threshold decision field, 30: three-dimensional original image, 31 target pixel, 33 and 33a: determination range (pixels around the target pixel), 7: density value histogram, 70: density value histogram peak, 71a and 71b: distribution curve, 72: symmetrical distribution curve, 73: subtracted distribution value, t1/t2/t3: threshold

The invention claimed is:

1. An image processing apparatus including a processor and a non-transitory storage medium storing one or more programs of instructions which are executable by the processor to perform and to configure the host computer to comprise a process to recognize a specific region from an image and to configure the apparatus to comprise:
a threshold determination unit performing threshold determination for a determination range including a target pixel and multiple pixels surrounding the target pixel among pixels included in the image by applying predetermined threshold conditions to specify the target pixel as a recognized pixel in a case where the threshold conditions are satisfied in any pixel within the determination range;
a process execution unit executing the threshold determination repeatedly by moving the determination range sequentially; and
a threshold automatic calculation unit that calculates a peak position of a density value distribution histogram of the image, calculates a symmetrical distribution curve that is symmetrical about the peak position using data of a part whose density value is lower than the peak position, subtracts the symmetrical distribution curve from a distribution curve of the histogram to calculate a subtracted distribution curve, and calculates the threshold conditions based on the subtracted distribution curve,
wherein the threshold determination unit applies the threshold conditions calculated by the threshold automatic calculation unit to perform the threshold determination.

2. The image processing apparatus according to claim 1, wherein the threshold determination unit applies different threshold conditions between (i) pixels on a same flat surface with the target pixel and (ii) pixels on another flat surface to specify the target pixel as the recognized pixel in a case where it was determined that the threshold conditions were satisfied in any pixel within the determination range.

3. The image processing apparatus according to claim 2, wherein the different thresholds are set according to a distance from the target pixel as the threshold conditions.

4. The image processing apparatus according to claim 1, wherein the threshold determination unit applies the same threshold conditions to all the pixels within the determination range to specify the target pixel as the recognized pixel in a case where it was determined that the threshold conditions were satisfied in any pixel.

5. The image processing apparatus according to claim 1, further comprising:
a threshold manual setting unit allowing an operator to set the threshold conditions,
wherein the threshold determination unit applies threshold determination set by the threshold manual setting unit to perform the threshold determination.

6. The image processing apparatus according to claim 1, further comprising:
a processing mode selection unit selecting whether to perform threshold determination for the single target pixel, whether to perform threshold determination for all the pixels included in the determination range using the same threshold conditions, or whether to perform threshold determination between (i) pixels on a same flat surface with the target pixel and (ii) pixels on another flat surface using different threshold conditions as a processing mode in the threshold determination.

7. The image processing apparatus according to claim 1, further comprising:
a threshold setting method selection unit selecting whether to allow an operator to manually set the threshold conditions or whether to calculate the threshold conditions based on a density value distribution histogram of the image,
wherein the threshold determination unit sets the threshold conditions using a method selected by the threshold setting method selection unit.

8. The image processing apparatus according to claim 1, further comprising:
a diagnostic image generation unit generating a diagnostic image in which a recognized pixel recognized by the threshold determination unit was eliminated or extracted from the image.

9. An image processing method recognizing a specific region from an image using a computer, the method performed by the computer comprising:
(a) performing threshold determination for a determination range including a target pixel and multiple pixels surrounding the target pixel among pixels included in the image by applying predetermined threshold conditions to specify the target pixel as a recognized pixel in a case where the threshold conditions are satisfied in any pixel within the determination range;
(b) executing the threshold determination repeatedly by moving the determination range sequentially; and
(c) calculating a peak position of a density value distribution histogram of the image, calculating a symmetrical distribution curve that is symmetrical about the peak position using data of a part whose density value is lower than the peak position, subtracting the symmetrical distribution curve from a distribution curve of the histogram to calculate a subtracted distribution curve, and calculating the threshold conditions based on the subtracted distribution curve, wherein the threshold conditions calculated in (c) are applied to perform the threshold determination in (a).

* * * * *